US006022527A

United States Patent [19]

Boucher, Jr. et al.

[11] Patent Number: 6,022,527

[45] Date of Patent: Feb. 8, 2000

[54] METHOD OF TREATING LUNG DISEASES WITH URIDINE 5'-DIPHOSPHATE AND ANALOGS THEREOF

[75] Inventors: Richard C. Boucher, Jr.; Sammy Ray Shaver, both of Chapel Hill; William Pendergast, Durham; Benjamin Yerxa; Janet L. Rideout, both of Raleigh; Robert Dougherty, Chapel Hill; Dallas Croom, Apex, all of N.C.

[73] Assignees: The University of North Carolina at Chapel Hill, Chapel Hill; Inspire Pharmaceuticals, Inc., Durham, both of N.C.

[21] Appl. No.: 09/352,390

[22] Filed: Jul. 13, 1999

Related U.S. Application Data

[62] Division of application No. 09/143,297, Aug. 28, 1998.
[60] Provisional application No. 60/057,064, Aug. 29, 1997.

[51] Int. Cl.[7] .......... A61K 9/12

[52] U.S. Cl. .......... 424/45; 424/46; 514/851; 514/826

[58] Field of Search .......... 424/45, 46, 489; 514/851, 826

[56] References Cited

U.S. PATENT DOCUMENTS

| | | | |
|---|---|---|---|
| 3,313,813 | 4/1967 | Cragoe et al. | 260/250 |
| 3,846,402 | 11/1974 | Eckstein et al. | 260/211.5 |

(List continued on next page.)

FOREIGN PATENT DOCUMENTS

| | | |
|---|---|---|
| 25 30 862 | 1/1976 | Netherlands . |
| 92/11016 | 7/1992 | WIPO . |

OTHER PUBLICATIONS

Eric A. Barnard; Hexokinases from Yeast, *Methods in Enzymology* 42:6–20 (1975).

(List continued on next page.)

*Primary Examiner*—Raj Bawa

*Attorney, Agent, or Firm*—Myer Bigel Sibley & Sajovec

[57] ABSTRACT

Compounds of Formula I:

(I)

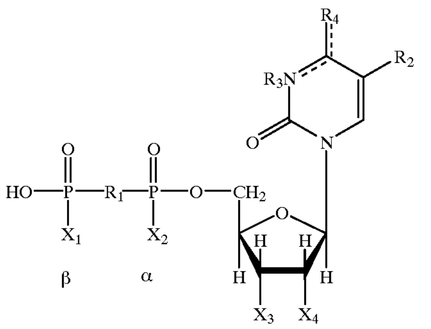

wherein:

$X_1$, and $X_2$ are each independently either $O^-$ or $S^-$;

$X_3$ and $X_4$ are each independently either —H or —OH, with the proviso that $X_3$ and $X_4$ are not simultaneously —H;

$R_1$ is selected from the group consisting of O, imido, methylene and dihalomethylene;

$R_2$ is selected from the group consisting of H, halo, alkyl, substituted alkyl, alkoxyl, nitro and azido;

$R_3$ is selected from the group consisting of H, alkyl, acyl, aryl, and arylalkyl; and $R_4$ is selected from the group consisting of —OR', —SR', —NR', and —NR'R", wherein R' and R" are independently selected from the group consisting of H, alkyl, substituted alkyl, aryl, substituted aryl, arylalkyl, alkoxyl, and aryloxyl, with the proviso that R' is absent when $R_4$ is double bonded from an oxygen or sulfur atom to the carbon at the 4-position of the pyrimidine ring, are used in methods of hydrating lung mucus secretions and treating lung disorders such as cystic fibrosis, ventilator-associated pneumonia, chronic bronchitis, chronic obstructive pulmonary disorder and primary ciliary dyskinesia. Pharmaceutical compositions containing compounds of Formula I, and novel compounds of Formula I are also described.

24 Claims, 6 Drawing Sheets

U.S. PATENT DOCUMENTS

| | | | |
|---|---|---|---|
| 4,501,729 | 2/1985 | Boucher et al. | 424/45 |
| 5,292,498 | 3/1994 | Boucher, Jr. | 424/45 |
| 5,420,116 | 5/1995 | Puchelle et al. | 514/47 |
| 5,628,984 | 5/1997 | Boucher, Jr. | 424/45 |
| 5,635,160 | 6/1997 | Stutts, III et al. | 424/45 |
| 5,656,256 | 8/1997 | Boucher et al. | 424/45 |

OTHER PUBLICATIONS

Brown et al.; Evidence that UTP and ATP Regulate Phospholipase C through a Common Extracellular 5'–Nucleotide Receptor in Human Airway Epithelial Cells, *Molecular Pharmacology* 40:648–655.

Chang et al.; Molecular Cloning and Functional Analysis of a Novel $P_2$ Nuecloetide Receptor, *The Journal of Biological Chemistry,* 270, No. 44:26152–26158.

S.H. Donaldson et al; In Vivo Regulation of ATP Levels in Human Nasal Epithelia, *Pediatric Pulmonology Supp.;* 13, 290 (Abstract No. 286) (1996).

Erb et al; Site–directed Mutagenesis of $P_{2u}$ Purinoceptors, *The Journal of Biological Chemistry* 270:4185–4188 (1995).

Goody et al; Thiophasphate Analogs of Nucleoside Di– and Triphosphates, *Journal of the American Chemical Society* 93:6252–6258 (1971).

Knowles et al., Activation by Extracellular Nucleotides of Chloride Secretion in the Airway Epithelia of Patients with Cystic Fibrosis, *New England Journal of Medicine,* 325:533–538 (Aug. 22, 1991).

Knowles et al; Extracellular ATP and UTP Induce Chloride Secretion in Nasal Epithelia of Cystic Fibrosis Patients and Normal Subject in vivo, *Chest* 101:60S–63S (Mar. 1992 Supplement).

Knowles et al; Abnormal Ion Permeation Through Cystic Fibrosis Respiratory Epithelium *Science* 221:1067–1069 (1983).

Knowles et al; Relative Ion Permeability of Normal and Cystic Fibrosis Nasal Epithelium, *J. Clinical Invest.* 71:1410–1417 (May 1983).

Larsen et al; Cation Transport by Sweat Ducts in Primary Culture, Ionic Mechanism of Cholinergically Evoked Current Oscillations *Journal of Physiology* 424:109–131 (1990).

Lazarowski et al; Identification of a Uridine Nucleotide–selective G–protein–linked Receptor that Activates Phospholipase C, *The Journal of Biological Chemistry* 269(11830–11836) (1994).

Lazarowski et al; Pharmacological selectivity of the cloned human $P_{2u}$–puriniceptor potent activation by diadenosine tetraphosphate *Br. J. Pharmacol.* 116:1619–1627 (1995).

Lazarowski et al; Enzymatic synthesis of $UTP_{\gamma}S$, a potent hydrolysis resistant agonist of $P_{2u}$–purinoreceptors, *British Journal of Pharmacology* 117:203–209 (1996).

Lazarowski et al; Mucosal–Restricted $P_{2u}$–Receptor Independent Action of UDP on Human Nasal Epithelial Cells; *Pediatric Pulmonology* Supp 13, 290 (Abstract No. 292) (1996).

Nakahata et al.; Regulation of inositol triphosphate accumulation by muscarinic cholinergic and $H_1$–histamine receptors on human astrocytoma cells, *Biochem J.* 241:337–344 (1987).

Mason et al; Regulation of transepithelial ion transport and intracellular calcium by extracellular ATP in human normal and cystic fibrosis airway epithelium *Br. J. Pharmacol.* 103:1649–1656 (1991).

Nicholas et al; Uridine Nucleotide Selectivity of Three Phospholipase C–Activating $P_2$ Receptors: Identification of a UDP–Selective, a UTP–Selective, and an ATP– and UTP–Specific Receptor *Molecular Pharmacology,* 50:224–229 (1996).

Olivier et al.; Acute Safety and Effects on Mucociliary Clearance of Aerosolized Uridine 5'–Triphosphate ±Amiloride in Normal Human Adults *Am j Respir Crit Care Med* 154:217–223 (1996).

Paradiso et al; Membrane–restricted regulation of $Ca^{2+}$ release and influx in polarized epithelia *Nature* 377:643–646 (Oct. 19, 1995).

Parr et al; Cloning and expression of a human $P_{2u}$ nucleotide receptor, a target for cystic fibrosis pharmacotherapy *Proc. Natl. Acad. Sci. USA* 91:3275–3279 (Apr. 1994).

Stutts et al; Multiple modes of regulation of airway epithelial chloride secretion by extracellular ATP *American Physiological Society* 267:C1442–C1451 (1994).

Wu et al; Growth and Differentiation of Human Nasal Epithelial Cells in Culture, *Am Rev Respir Dis* 132:311–320 (1985).

Mucociliary Clearance in Sheep

METHOD OF TREATING LUNG DISEASES WITH URIDINE 5'-DIPHOSPHATE AND ANALOGS THEREOF

RELATED APPLICATIONS

This application is a divisional of U.S. application Ser. No. 09/143,297, filed Aug. 28, 1998, the disclosure of which is incorporated herewith in its entirety.

This application claims the benefit of filing of U.S. Provisional Application No. 60/057,064, filed Aug. 29, 1997, which application is incorporated herein in its entirety.

GOVERNMENT SUPPORT

This invention was made with United States government support under grant number #2PO1 HL32322-11A1 from the National Institutes of Health. The United States government has certain rights in this invention

FIELD OF THE INVENTION

This invention relates to methods of treating lung disease, and novel compounds and pharmaceutical compositions useful therefor.

BACKGROUND OF THE INVENTION

One therapeutic goal in cystic fibrosis and other pulmonary diseases in which the water content of lung mucus is altered is to hydrate the lung mucus secretions, so that the secretions may thereafter be more easily removed from the lungs by mucociliary action or simple coughing. For example, the use of aerosolized amiloride to hydrate mucus secretions is described in U.S. Pat. No. 4,501,729 to Boucher et al. Amiloride appears to block $Na^+$ reabsorption by airway epithelial cells, and therefore inhibits water absorption from the mucus. While an important breakthrough in providing treatments for cystic fibrosis, a potential problem with amiloride as a therapeutic is its relatively short duration of action.

In certain lung diseases (e.g., cystic fibrosis), several functions of airway epithelia are abnormal, and deficiencies in both $Cl^-$ transport and $Na^+$ absorption are well documented. See, e.g. Knowles et al., *Science* 221, 1067 (1983); Knowles et al., *J. Clin. Invest.* 71, 1410 (1983). Regulation of ion transport is thus thought to have potential therapeutic benefit in lung diseases characterized by abnormalities in epithelial ion transport. Confirmation of the presence of $P2Y_2$ ($P_{2U}$-purinergic) receptors on the apical surface of human airway epithelial cells raised the possibility that aerosolized nucleotides might be used therapeutically to induce $Cl^-$ secretion in individuals with cystic fibrosis or other airway diseases. Accordingly, a different therapeutic approach for hydrating lung mucus secretions is exemplified by techniques that involve the administration of ATP or UTP, which appear to stimulate chloride secretion from respiratory epithelial cells. See, e.g., U.S. Pat. No. 5,292,498 to Boucher.

Existence of a G-protein-coupled receptor that selectively recognizes uridine 5'-diphosphate (UDP) was originally established in studies of a receptor natively expressed by C6-2B rat glioma cells. E. R. Lazarowski et al. *J. Biol. Chem.* 269, 11830–11836 (1994). The $P2Y_6$ receptor was recently cloned by K. Chang et al., *J. Biol. Chem.* 270, 26152–26158 (1995). This receptor was subsequently shown to be selectively activated by UDP, and to be the UDP receptor natively expressed in C6-2B cells. R. A. Nicholas et al., *Mol. Pharmacol.* 50, 224–229 (1996) The failure to identify this receptor in previous studies of mammalian tissues likely has been a consequence of the lack of availability of potent selective agonists for uridine nucleotide receptors, and the low chemical and metabolic stability of the available nucleotides. It was originally reported that UDP stimulated inositol phosphate accumulation in human airway epithelial cells by low potency activation of the $P2Y_2$ receptor. E. R. Lazarowski et al. *Br. J. Pharmacol.* 116, 1619–1627 (1995); H. A. Brown et al., *Mol. Pharmacol.* 40, 648–655 (1991). However, it has been recently demonstrated that UDP is in fact not an agonist at the $P2Y_2$ receptor (Nicholas et al., supra) and that the previously observed effect of UDP at $P2Y_2$ receptors can be explained by the presence of small amounts of contaminating UTP in UDP solutions and/or by conversion of UDP to UTP by cell surface nucleoside diphosphokinase.

Despite the evidence related to the $P2Y_6$ receptor and its relationship to UDP, it has heretofore not been recognized that this relationship may be useful in the treatment of airway disease.

SUMMARY OF THE INVENTION

The present inventors have discovered that the $P2Y_6$ receptor, which selectively recognizes UDP as a potent agonist, also exists in airway tissue. The association of the $P2Y_6$ receptor with increases in $Cl^-$ secretion indicates that UDP and other receptor-selective drugs that derive from this molecule are of therapeutic value in the treatment of a variety of airway diseases. Accordingly, a first aspect of the present invention relates to a method of hydrating mucus secretions in the lungs of a subject in need of such treatment. The method comprises administering to the lungs of the subject a compound of Formula I below, or a pharmaceutically acceptable salt thereof (hereinafter referred to as the "active compound"), in an amount effective to hydrate lung mucus secretions:

(I)

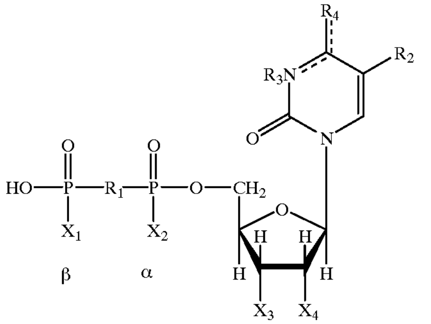

wherein:

$X_1$, and $X_2$ are each independently either $O^-$ or $S^-$;

$X_3$ and $X_4$ are each independently either —H or —OH, with the proviso that $X_3$ and $X_4$ are not simultaneously —H;

$R_1$ is selected from the group consisting of O, imido, methylene, and dihalomethylene (e.g., dichloromethylene, difluoromethylene);

$R_2$ is selected from the group consisting of H, halo, alkyl, substituted alkyl, alkoxyl, nitro and azido;

$R_3$ is selected from the group consisting of H, alkyl, acyl (including arylacyl), and arylalkyl; and $R_4$ is selected from the group consisting of —OR', —SR', NR', and NR'R", wherein R' and R" are independently selected from the group consisting of H, alkyl, substituted alkyl aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring.

The method of the present invention may further comprise the step of concurrently administering amiloride, benzarnil, or phenamil to the subject in an amount effective to inhibit the reabsorption of water from lung mucus secretions.

The method of the present invention is useful in treating several disorders of the lung, including but not limited to, cystic fibrosis, chronic bronchitis, chronic obstructive pulmonary disorder (COPD), primary ciliary dyskinesia, and ventilator-associated pneumonia (VAP).

A second aspect of the present invention is a pharmaceutical composition containing the active compounds disclosed herein, in an amount effective to hydrate lung mucus secretions, in a pharmaceutically acceptable carrier.

Novel compounds useful in the treatment of lung disorders are a third aspect of the present invention. These compounds have the structure of Formula I as set forth above, with the proviso that such novel compounds do not include the known compounds uridine 5'-diphosphate (or UDP), 2-deoxyuridine 5'-diphosphate (or dUDP), uridine 5'-O-(2-thiodiphosphate) (or UDP-β-S), and 4-mercaptouridine 5'-diphosphate (or 4-mercaptoUDP). Novel compounds of the present invention include, but are not limited to, 3'-deoxyuridine 5'-diphosphate; 5-bromouridine 5'-diphosphate; 5-(1-phenylethynyl)-uridine 5'-diphosphate; 5-methyluridine 5'-diphosphate; 4-hexylthiouridine 5'-diphosphate; 4-methoxyuridine 5'-diphosphate; 4-(N-morpholino)uridine 5'-diphosphate; 4-hexyloxyuridine 5'-diphosphate; N,N-dimethylcytidine 5'-diphosphate; N-hexylcytidine 5'-diphosphate; and N-cyclopentylcytidine 5'-diphosphate.

A fourth aspect of the present invention is the use of the active compounds described herein for the manufacture of a medicament for the therapeutic hydration of mucus secretions in the lungs of a subject in need of such treatment.

BRIEF DESCRIPTION OF THE DRAWINGS

FIG. 3 also illustrates the effects if UTP and UDP on intracellular calcium mobilization in polarized human nasal epithelial cells. Confluent cells were loaded with $[^3H]$myo-inositol and preincubated with LiCl (FIG. 3A), or with Fura-2 (FIG. 3B), as described below in Examples 2 and 3. The cells were challenged with 100 μM of either UTP (left-hand pair of data bars) or UDP (right-hand set of data bars), added to either the serosal (open bars) or the mucosal (filled-in bars) medium. The data in FIG. 3A are shown as the concentration of $[^3H]$inositol phosphate in units of cpm×$10^{-3}$ and represent the medium (±S.E.M.) from three experiments performed with triplicates. The data in FIG. 3B are shown as $\Delta Ca^{2+}{}_i$ in units of μM, and represent the medium (±S.E.M.) from fourteen individual experiments.

DETAILED DESCRIPTION OF THE INVENTION

Figure 1:
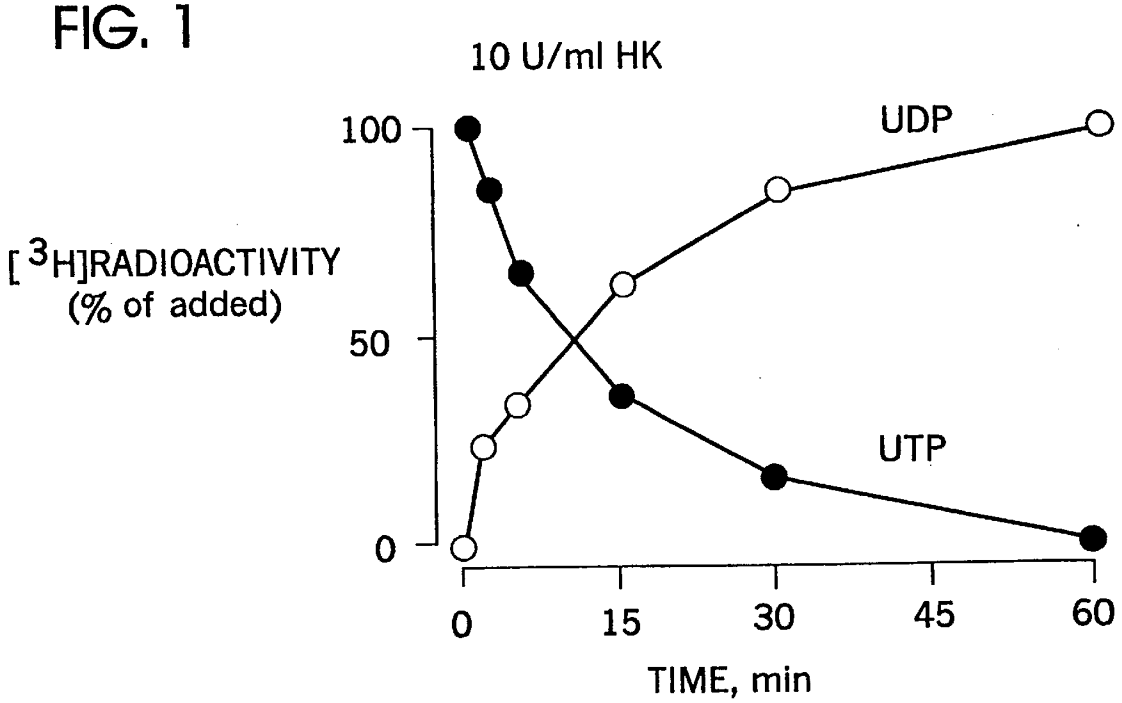
FIG. 1 is a graph showing the time course for the conversion of $[^3H]$UTP to $[^3H]$UDP in the presence of 10 units/mL hexokinase (HK). The data is expressed as the percentage of $[^3H]$uridine triphosphate converted to $[^3H]$ uridine diphosphate with open circles (○) indicating the relative amount of $[^3H]$uridine diphosphate , while filled-in circles (●) indicate the related amount of $[^3H]$uridine triphosphate. The data indicate the mean value of one experiment representative of two independent experiments performed with duplicate samples that differed by less than 20%.

The methods and pharmaceutical formulations of the present invention can be used to facilitate (i.e., enhance, speed, assist) the clearance of mucus secretions from the lungs of a subject in need of such treatment for any reason, including (but not limited to) retained secretions arising from airway diseases such as cystic fibrosis, chronic bronchitis, chronic obstructive pulmonary disorder (COPD), ventilator-associated pneumonia (VAP), primary ciliary dyskinesia, asthma, bronchiectasis, post-operative atelectasis (plugging of airways with retained secretions after surgery), and Kartagener's syndrome.

The present invention is concerned primarily with the treatment of human subjects, but may also be employed for the treatment of other mammalian subjects, such as dogs and cats, for veterinary purposes.

The methods of the present invention include the administration of compounds of Formula I, while pharmaceutical compositions of the present invention comprise compounds of Formula I. As used herein, a compound of Formula I is as follows:

(I)

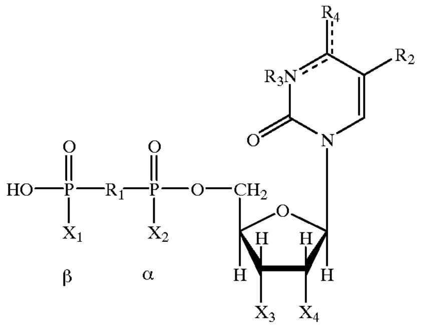

wherein:

$X_1$, and $X_2$ are each independently either $O^-$ or $S^-$;

$X_3$ and $X_4$ are each independently either —H or —OH, with the proviso that $X_3$ and $X_4$ are not simultaneously —H;

$R_1$ is selected from the group consisting of O, imido, methylene, and dihalomethylene (e.g., dichloromethylene, difluoromethylene);

$R_2$ is selected from the group consisting of H, halo, alkyl, substituted alkyl, alkoxyl, nitro and azido;

$R_3$ is selected from the group consisting of H, alkyl, acyl (including arylacyl), and arylalkyl; and $R_4$ is selected from the group consisting of —OR', —SR', NR', and NR'R", wherein R' and R" are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring.

As used herein the term "alkyl" refers to $C_{1-10}$ inclusive, linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. As used herein, the term "acyl" refers to an organic acid group wherein the —OH of the carboxyl group has been replaced with another substituent (i.e., as represented by RCO—, wherein R is an alkyl or an aryl group). As such, the term "acyl" specifically includes arylacyl groups. Specific examples of acyl groups include acetyl and benzoyl. As used herein, the term "aryl" refers to 5 and 6-membered hydrocarbon and heterocyclic aromatic rings. Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like. The term "alkoxyl" as used herein refers to $C_{1-10}$ inclusive, linear, branched, or cyclic, saturated or unsaturated oxo-hydrocarbon chains, including for example methoxy, ethoxy, propoxy, isopropoxy, butoxy, t-butoxy, and pentoxy. The term "aryloxyl" as used herein refers to phenyloxyl or hexyloxyl, and alkyl, halo, or alkoxyl substituted phenyloxyl or hexyloxyl. As used herein, the terms "substituted alkyl" and "substituted aryl" include alkyl and aryl groups, as defined herein, in which one or more atoms or functional groups of the aryl or alkyl group are replaced with another atom or functional group, including for example, halogen, aryl, alkyl, alkoxy, hydroxy, nitro, amino, alkylamino, dialkylamino, sulfate, and mercapto. The terms "halo," "halide," or "halogen" as used herein refer to fluoro, chloro, bromo, and iodo groups.

Compounds illustrative of the compounds of Formula (I) above include: uridine 5'-diphosphate (also referred to herein as UDP); uridine 5'-O-(2-thiodiphosphate) (also referred to herein as UDP-β-S); 2-deoxyuridine 5'-diphosphate (also referred to herein as dUDP); 3'-deoxyuridine 5'-diphosphate (also referred to herein as 3'-deoxyUDP); 5-bromouridine 5'-diphosphate (also referred to herein as 5-BrUDP); 5-(1-phenylethynyl)-uridine 5'-diphosphate (also referred to herein as 5-(1-phenylethynyl)UDP); 5-methyluridine 5'-diphosphate (also referred to herein as 5-methylUDP); 4-hexylthiouridine 5'-diphosphate (also referred to herein as 4-hexylthioUDP); 4-mercaptouridine 5'-diphosphate (also referred to herein as 4-mercaptoUDP); 4-methoxyuridine 5'-diphosphate (also referred to herein as 4-methoxyUDP); 4-(N-morpholino) uridine 5'-diphosphate (also referred to herein as 4-(N-morpholino)UDP; 4-hexyloxyuridine 5'-diphosphate (also referred to herein as 4-hexyloxyUDP); N,N-dimethylcytidine 5'-diphosphate (also referred to herein as N,N-dimethylCDP); N-hexylcytidine 5'-diphosphate (also referred to herein as N-hexylCDP); and N-cyclopentylcytidine 5'-diphosphate (also referred to herein as N-cyclopentylCDP). Certain compounds of Formula I (e.g., UDP, dUDP, UDP-β-S, and 4-mercaptoUDP) are known and may be made in accordance with known procedures or variations thereof, which will be apparent to those skilled in the art. For example, the identification and preparation of certain thiophosphate analogues of nucleoside diphosphates (such as UTP-β-S) are set forth in U.S. Pat. No. 3,846,402 to Eckstein et al., and in R. S. Goody and F. Eckstein, *J. Am. Chem. Soc.* 93, 6252–6257 (1971). Alternatively, UDP, dUDP, and other analogs thereof are also commercially available from vendors such as Sigma (St. Louis, Mo.) and Pharmacia (Uppsala, Sweden).

Other compounds of Formula I useful in the present invention (e.g., 5-(1-phenylethynyl)UDP; 3'-deoxyUDP, 5-methylUDP; 4-hexylthioUDP; 4-methoxyUDP; 4-hexyloxyUDP; 4-(N-morpholino)UDP; N,N-dimethylCDP; N-hexylCDP; and N-cyclopentylCDP) are novel compounds disclosed for the first time herein, and as such are claimed accordingly in the appended claims.

For the sake of simplicity, Formula I herein illustrates uridine diphosphate active compounds in the naturally occurring D configuration, but the present invention also encompasses compounds in the L configuration, and mixtures of compounds in the D and L configurations, unless otherwise specified. The naturally occurring D configuration is preferred.

The active compounds of Formula (I) may be administered by themselves or in the form of their pharmaceutically acceptable salts, e.g., an alkali metal salt such as sodium or potassium, an alkaline earth metal salt, or an ammonium and tetraalkyl ammonium salt, $NX_4^+$ (wherein X is a $C_{1-4}$ alkyl group). Pharmaceutically acceptable salts are salts that retain the desired biological activity of the parent compound and do not impart undesired toxicological effects.

Active compounds of the present invention may optionally be administered in conjunction with other compounds useful in the hydration of lung mucus secretions or useful in the facilitation of the removal of lung mucus secretions. Such compounds (herein referred to as "supplemental compounds") include, but are not limited to, benzamil, phenamil, and amiloride. Amiloride (also known as 3,5,-diamino-6-chloro-N-(diaminomethylene) pyrazinecarboxamide), benzamil (also known as 3,5-diamino-6-chloro-N-(benzylaminoaminomethylene) pyrazinecarboxamide) and phenamil (also known as 3,5-diamino-6-chloro-N-(phenylaminoaminomethylene) pyrazinecarboxamide) are known compounds and are disclosed in U.S. Pat. No. 3,313,813 to E. Cragoe. The terms "amiloride," "benzamil," and "phenamil," as used herein include the pharmaceutically acceptable salts thereof, such as (but not limited to) amiloride hydrochloride, benzamil hydrochloride or phenamil hydrochloride. Arniloride, benzamil or phenamil used to prepare compositions for the present invention may alternatively be in the form of a pharmaceutically acceptable free base of amiloride, benzamil or phenamil. In one embodiment of the invention, the supplemental compound is concurrently administered with the active compound or compounds of the present invention. As used herein, the word "concurrently" means sufficiently close in time to produce a combined (e.g., additive or synergistic) effect. In other words, concurrently may be defined as simultaneously, or it may be defined as two or more events occurring within a short time period before or after each other.

The active and supplemental compounds described herein may be administered to the lungs of a patient by any suitable means, but are preferably administered by administering an aerosol suspension of respirable particles comprised of the active compound, which the subject inhales. The active compound can be aerosolized in a variety of forms, such as, but not limited to, dry powder inhalants, metered dose inhalants, or liquid/liquid suspensions. The respirable particles may be liquid or solid. The quantity of active compound included may be an amount sufficient to achieve dissolved concentrations of active compound on the airway surfaces of the subject of from about $10^{-9}$ to about $10^{-1}$ Moles/liter, and more preferably from about $10^{-6}$ to about $10^{-4}$ Moles/liter.

The particulate pharmaceutical composition may optionally be combined with a carrier to aid in dispersion or transport. A suitable carrier such as a sugar (i.e., lactose, sucrose, trehalose, mannitol) may be blended with the active compound or compounds in any suitable ratio (e.g., a 1 to 1 ratio by weight).

Solid or liquid particulate forms of the active compound prepared for practicing the present invention should include particles of respirable size: that is, particles of a size sufficiently small to pass through the mouth and larynx upon inhalation and into the bronchi and alveoli of the lungs. In general, particles ranging from about 1 to 10 microns in size are within the respirable range. Particles of non-respirable size which are included in the aerosol tend to be deposited in the throat and swallowed, and the quantity of non-respirable particles in the aerosol is preferably minimized.

The dosage of active compound will vary depending on the condition being treated and the state of the subject, but generally may be an amount sufficient to achieve dissolved concentrations of active compound on the airway surfaces of the subject of from about $10^{-9}$ to about $10^{-1}$ Moles/liter, and more preferably from about $10^{-6}$ to about $10^{-4}$ Moles/liter. Depending upon the solubility of the particular formulation of active compound administered, the daily dose may be divided among one or several unit dose administrations. The daily dose by weight will depend upon the age and condition of the subject. Such a daily dose may be as low as 1 mg per day, under certain circumstances may be as low as 0.5 mg per day, and may even be as low as 0.1 mg/day. The daily dose of the active compounds may also be as high as 200 mg/day, under certain conditions may be as high as 500 mg/day, and may even be as high as 1000 mg/day. The doses of the active compounds may be provided as one or several prepackaged units.

In the manufacture of a formulation according to the invention, active compounds of the present invention or the pharmaceutically acceptable salts or free bases thereof are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation which may contain from 0.5% to 99% by weight of the active compound. One or more active compounds may be incorporated in the formulations of the invention, which formulations may be prepared by any of the well-known techniques of pharmacy consisting essentially of admixing the components.

Aerosols of liquid particles comprising the active compound may be produced by any suitable means, such as with a pressure-driven aerosol nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution, preferably made isotonic but may be hypertonic with body fluids by the addition of, for example, sodium chloride. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant.

During use these devices discharge the formulation through a valve adapted to deliver a metered volume, typically from 10 to 200 μl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidants and suitable flavoring agents.

Any propellant may be used in carrying out the present invention, including both chlorofluorocarbon-containing propellants and non-chlorofluorocarbon-containing propellants. Thus, fluorocarbon aerosol propellants that may be employed in carrying out the present invention including fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Examples of such propellants include, but are not limited to: $CF_3$—CHF—$CF_2$H; $CF_3$—$CH_2$—$CF_2$H; $CF_3$—CHF—$CF_3$; $CF_3$—$CH_2$—$CF_3$; $CF_3$—CHCl—$CF_2$Cl; $CF_3$—CHCl—$CF_3$; cy—C($CF_2$)$_3$—CHCl; $CF_3$—CHCl—$CH_2$Cl; $CF_3$—CHF—$CF_2$Cl; $CF_3$—CHCl—CFHCl; $CF_3$—CFCl—CFHCl; $CF_3$—$CF_2$—$CF_2$H; $CF_3$—$CF_2$—$CH_3$; $CF_2$H—$CF_2$—$CFH_2$; $CF_3$—$CF_2$—$CFH_2$; $CF_3$—$CF_2$—$CH_2$Cl; $CF_2$H—$CF_2$—$CH_3$; $CF_2$H—$CF_2$—$CH_2$Cl; $CF_3$—$CF_2$—$CF_2$—$CH_3$; $CF_3$—$CF_2$—$CF_2$—$CF_2$H; $CF_3$—CHF—CHF—$CF_3$; $CF_3$—O—$CF_3$; $CF_3$—O—$CF_2$H; $CF_2$H—H—O—$CF_2$H; $CF_2$H—O—$CFH_2$; $CF_3$—O—$CH_3$; $CF_3$—O—$CF_2$—$CF_2$H; $CF_3$—O—$CF_2$—O—$CF_3$; cy—$CF_2$—$CF_2$—O—$CF_2$—; cy—CHF—$CF_2$—O—$CF_2$—; cy—$CH_2$—$CF_2$—O—$CF_2$—; cy—$CF_2$—O—$CF_2$—O—$CF_2$—; $CF_3$—O—$CF_2$—Br; $CF_2$H—O—$CF_2$—Br; and mixtures thereof, where "cy" denotes a cyclic compound in which the end terminal covalent bonds of the structures shown are the same so that the end terminal groups are covalently bonded together. Particularly preferred are hydrofluoroalkanes such as 1,1,1,2-tetrafluoroethane (propellant 134a) and heptafluoropropane (propellant 227). A stabilizer such as a fluoropolyrner may optionally be included in formulations of fluorocarbon propellants, such as described in U.S. Pat. No. 5,376,359 to Johnson.

Compositions containing respirable dry particles of micronized active compound of the present invention may be prepared by grinding the dry active compound with, e.g., a mortar and pestle or other appropriate grinding device, and then passing the micronized composition through a 400 mesh screen to break up or separate out large agglomerates.

The aerosol, whether formed from solid or liquid particles, may be produced by the aerosol generator at a rate of from about 10 to 150 liters per minute. Aerosols containing greater amounts of medicament may be administered more rapidly. Typically, each aerosol may be delivered to the patient for a period from about 30 seconds to about 20 minutes, with a delivery period of about five to ten minutes being preferred.

The particulate composition comprising the active compound may optionally contain a carrier which serves to facilitate the formation of an aerosol. A suitable carrier is lactose, which may be blended with the active compound in any suitable ratio. Again, other therapeutic compounds such as amiloride, benzamil or phenamil may also be included.

If desired, the active compounds of the present invention may be concurrently administered with uridine 5'-triphosphate (UTP) or an analog thereof (including the pharmaceutically acceptable salts thereof), in an amount effective to stimulate chloride secretion from respiratory epithelial cells (and thereby further hydrate the lung mucus secretions). Formulations containing amiloride, benzamil or phenamil may also contain UTP or an analog thereof in an amount effective to stimulate chloride secretion from respiratory epithelial cells. UTP and analogs thereof that may be used to carry out this technique are disclosed in U.S. Pat. No. 5,292,498 to Boucher.

The present invention is explained in greater detail in the Examples which follow. These examples are intended as illustrative of the invention, and are not to be taken as limiting thereof. In the following Examples, UTP and ATP were obtained from Pharmacia (Uppsala, Sweden), and UDP and hexokinase were from Boehringer Mannheim (Indianapolis, Ind.). [$^3$H]myo-inositol (20 Ci/mmol) was from ARC (St. Louis, Mo.) and [$^3$H]UTP and [$^3$H]ATP (97% and 99% pure, respectively) (17–20 Ci/mmol) were from Amersham (Arlington Heights, Ill.). The miniature perfusion chamber described herein was graciously provided by the staff of E. Larsen's laboratory (Zoophysiological Laboratory A, August Krogh Institute, University of Copenhagen, Denmark). Abbreviations used in the following Examples are as follows: °C. means degrees in Centigrade; h means hours; min means minutes; sec means seconds, nm means nanometers; g means grams, ng means nanograms, mg means milligrams, L means liter, mL means milliliter, mmole means millimoles, μmole means micromoles, Ci means curies, μCi means microcuries; and DMEM means Dulbecco's Modified Eagle's Medium.

EXAMPLE 1

Methods: Cell Cultures

Human nasal epithelial cells were harvested from turbinates using protease XIV (Sigma, St. Louis, Mo.) for 24–48 h at 4° C., as previously described. R. Wu, et al., *Am. Rev. Respir. Dis.* 132, 311–320 (1985). Cytosolic $Ca^{2+}$ and inositol phosphate measurements were made on nasal cell monolayers plated on porous Transwell Col filters (pore diameter 0.45 μm; Costar, Cambridge, Mass.) and maintained in Ham's F12 media supplemented with 10 ng/mL epidermal growth factor, 3.75 ng/mL endothelial cell growth factor, 500 ng/mL hydrocortisone, 5 ng/mL insulin, and 1 mM $CaCl_2$ (Ham's F12+4X medium). Assays were carried out 7 to 10 days after seeding, a time coincident with the development of the maximal transepithelial potential difference according to N. Nakahata & T. K. Harden, *Biochem. J.* 241, 33714 344 (1987).

EXAMPLE 2

Methods: Measurement of Inositol Phosphates

Confluent human nasal epithelial cells as described in Example 1 were labeled for 18 h in inositol-free DMEM containing 4.5 g/L glucose and 5 μCi/mL of [$^3$H]myo-inositol. These cells were pre-incubated with 10 mM LiCl and challenged with agonists for an additional 10 min. No changes of medium were made subsequent to addition of [$^3$H]myo-inositol to avoid release of endogenous ATP from stressed cells. E. R. Lazarowski et al., *Br. J Pharmacol.* 116, 1619–1627 (1995). Incubations were terminated by addition of 5% ice-cold trichloroacetic acid and the resultant [$^3$H] inositol phosphates were separated on Dowex AG1-X8 columns as described in A. M. Paradiso et al., *Nature* 377, 643–646 (1995).

EXAMPLE 3

Methods: Combined Bioelectric and Cytosolic $Ca^{2+}$ Measurements

Nasal cells grown on Transwell Col filters affixed to O-rings were maintained in F12+4X medium and studied 7–10 days after cell plating as described above. For $Ca^{2+}{}_i$ measurements, cells were loaded with Fura-2 and mounted in a miniature Ussing chamber over an objective of a microscope (Zeiss) coupled to a microfluorimeter, and cytosolic $Ca^{2+}{}_i$ levels were quantitated as previously described in Paradiso et al., supra. The fluorescence intensity ratio (excitation 340/380; emission λ 450 nm) was collected from a field of 30-40 nasal cells on monolayers and converted to $Ca^{2+}$ as previously described in E. H. Larsen et al, *J. Physiol.* 424, 109–131 (1990). For simultaneous measurements of $Cl^-$ secretion, the transepithelial potential difference (TEP) was measured by a Voltage-Clamp/Pulse Generator (Model VCC600, Physiologic Instruments, San Diego, Calif.) and recorded on a two-channel recorder (Linsesis Model L200S). To calculate changes in $Cl^-$ secretory current ($\Delta I_{Cl^-}$), a defined 1 sec current pulse was delivered across the monolayer every 10 sec. The nasal tissue was converted from its native $Na^+$ absorptive state to a $Cl^-$ secretory state by exposing monolayers to a luminal medium containing 0 $Na^+$/low $Cl^-$ and to a basolateral medium of Krebs bicarbonate Ringer solution.

EXAMPLE 4

Methods: Hydrolysis of [$^3$H]UTP and [$^3$H]UDP

Nasal monolayers were grown to confluence on 6.5 mm Transwells (Costar) as indicated above. The cells were washed twice and preincubated with 300 μl HEPES-buffered (pH, 7.4) DMEM medium for at least one hour prior to the addition of the [$^3$H]-nucleotides to ensure that any endogeneously released ATP was degraded. Incubations were initiated by addition of 2 μM [$^3$H]UTP or [$^3$H]UDP (0.5 μCi each) to either cell surface. Incubations were terminated at the indicated times by transferring the medium to a tube containing 30 μl 50 mM EDTA and boiled for 2 min.

EXAMPLE 5

Methods: Nucleoside Diphosphokinase (NDPK) Assay

To assay for the presence of ecto-NDPK activity, cells were incubated with [$^3$H]UDP as detailed above and ATP (100 μM) was included in the incubation medium. The ATP-dependent conversion of [$^3$H]UDP to [$^3$H]UTP was quantitated as described previously in E. R. Lazarowski et al., *Br. J. Pharmacol.* 117, 203–209 (1995).

EXAMPLE 6

Methods: HPLC Analysis

Nucleotides were separated by HPLC (Shimadzu Scientific Instruments, Inc., Columbia, Md.) via a strong anion exchange column (Rainin Instrument Co., Emeryville, Calif.) using a two solvent system consisting of buffer A (45 mM ammonium formate, pH 4.6) and buffer B (250 mM sodium phosphate, pH 2.7). A linear gradient was developed from 100% buffer A to 100% B during the first 25 min. The column then was eluted with 100% buffer B for the following 15 min and with 100% buffer A for an additional 15 min from 45 to 60 min. Absorbance at 260 nm was monitored with a LSA UV detector (Shimadzu), and radioactivity was monitored on-line with a Flo-One detector (Packard Instrument Co., Meridien, Conn.). [$^3$H]Nucleotides and [$^3$H] nucleosides were quantitated as previously described. Id.

EXAMPLE 7

Methods: Enzymatic Conversion of UTP to UDP

Accurate delineation of the pharmacological selectivities of nucleotide receptors is hampered by impurities frequently present in nucleotide solutions and by potential ecto-enzyme-catalyzed interconversion between triphospho- and diphosphonucleotides. Commercial preparations of UDP contain up to 2% UTP. Experiments were performed to evaluate the efficacy of hexokinase in converting UTP to UDP. It is known that in the presence of glucose, hexokinase transfers the γ-phosphate of ATP to glucose, producing ADP and glucose 6-phosphate as products. E. A. Barnard, *Meth. Enzymol.* 42, 6–20 (1975). Although ATP is the preferential substrate for hexokinase, other nucleoside triphosphates also serve as γ-phosphate donors although at slower rates of reaction. Id.

It was determined that incubation of 1 mM UTP with 10 U/mL hexokinase results in quantitative conversion of UTP to UDP. Incubations were carried out at 37° C. in 1 mL HEPES buffered DMEM medium (pH 7.4) containing 25 mM glucose and 1 mM (0.5 μCi) of either [$^3$H]ATP or [$^3$H]UTP. At the times indicated, 5 mM EDTA was added to the samples, followed by boiling. The results are expressed as the percent conversion of [$^3$H]nucleotide triphosphate to [$^3$H]nucleotide diphosphate. The data indicate the mean value of one experiment representative of two independent experiments performed with duplicate samples which differed by less than 20%.

In view of these results, and to ensure that no UTP contaminated UDP, stock solutions of UDP (1 mM) were routinely pre-incubated with 10 U/mL hexokinase and 25 mM glucose for 1 h prior to assays.

EXAMPLE 8

Methods: Synthesis of [$^3$H]UDP

[$^3$H]UDP was prepared by incubating [$^3$H]UTP with hexokinase and glucose followed by boiling for 2 min as indicated above.

EXAMPLE 9

Metabolism of [$^3$H]UDP and [$^3$H]UTP by Human Airway Epithelial Cell Surfaces Confluent polarized cells were incubated for 20 min at 37° C. in the presence of 1 μM (0.2 μCi) of [$^3$H]UTP, [$^3$H]UDP, or [$^3$H]UDP combined with 100 μM ATP. All additions were to the mucosal bath (300 μl final volume). Incubations were terminated by transferring the mucosal medium to an Eppendorf tube containing 30 μl 50 mM EDTA, followed by boiling. [$^3$H]Species were separated by HPLC as indicated in Example 6.

Figure 2A:
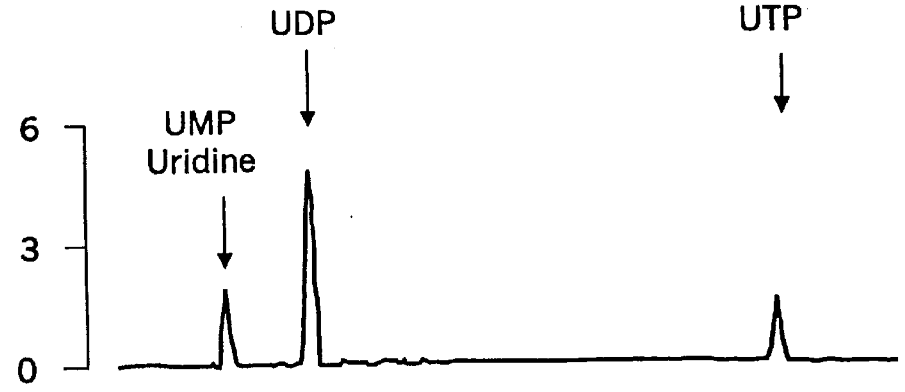
FIG. 2. illustrates, by means of three separate HPLC traces, the metabolism of $[^3H]$UTP and $[^3H]$UDP by human nasal epithelial cells. Each trace represents the results of experiments in which confluent, polarized human airway epithelial cells were incubated for 20 minutes at 37° C. in the presence of 1 μM (0.2 μCi) of $[^3H]$UTP (FIG. 2A), $[^3H]$UDP (FIG. 2B), and $[^3H]$UDP combined with 100 μM ATP (FIG. 2C). The traces shown in FIGS. 2A, 2B and 2C are representative of at least three independent experiments performed with duplicates. In each trace, the X-axis of the trace indicates elution time in minutes, while the Y-axis indicates the concentration of $[^3H]$ radioactivity in units of cpm×$10^{-3}$.
Figure 2B:
Figure 2C:
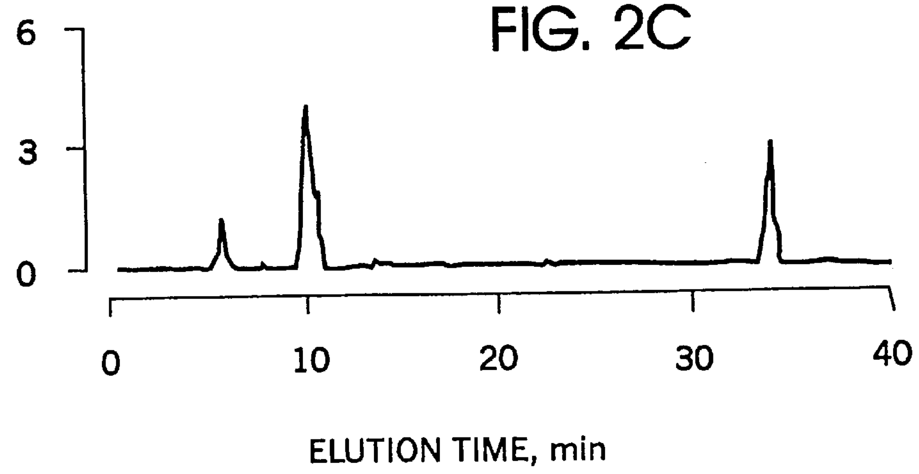

The results of this experiment are illustrated in the HPLC traces of FIG. 2A (incubation with [$^3$ H]UTP), FIG. 2B (incubation with [$^3$H]UDP), and FIG. 2C (incubation with [$^3$H]UDP combined with 100 μM ATP). Each trace is representative of at least three independent experiments performed with duplicates. Incubation of 1 μM [$^3$H]UTP for 20 min on the mucosal surface resulted in 73±16% hydrolysis, indicating the presence of ecto-nucleotidases and/or phosphatases. [$^3$H]UDP accumulated as the major breakdown product of [$^3$H]UTP , as shown in FIG. 2A. Mucosal [$^3$H]UDP (1 μM) was also hydrolyzed, although to a lesser extent than [$^3$H]UTP, as shown in FIG. 2B. Time course experiments indicated that the half life (t½) values for mucosal [$^3$H]UTP and [$^3$]UDP were 14±2 min and 27±3 min, respectively (not shown).

Hydrolysis of both [$^3$H]UTP and [$^3$H]UDP on the surface of human nasal epithelial cells was determined on both cell surfaces by the following procedures: primary cultures of HNE cells were grown to confluence on 6.5 mm Transwells as a polarized epithelium. The cells were washed twice with pre-warmed DMEM-HEPES medium (pH 7.4), and were pre-incubated for 1 hour at 37° C. with 0.5 mL of medium added on each side. Incubations were initiated by the addition 50 μl of 10 μM (0.5 μCi) [$^3$H]UTP or [$^3$H]UDP on the indicated cell surface. Medium samples were collected during a 20 min incubation period and analyzed by HPLC as described in Example 6. The results from these experiments are summarized in Table 1 below. The values represent the mean (± range from the mean) from two experiments performed with duplicate samples.

| | Nucleotide Hydrolysis | |
|---|---|---|
| | MUCOSAL | SEROSAL |
| [$^3$H]UTP | 17 ± 22 | 98 ± 11 |
| [$^3$H]UDP | 87 ± 6 | 70 ± 9 |

Nucleoside diphosphokinase catalyzes the transfer of the γ-phosphate from nucleoside triphosphates to nucleoside diphosphates. It has been observed previously that the presence of a nucleoside diphosphokinase activity on the surface of 1321N1 human astrocytoma cells converts UDP (and ADP) to UTP (or ATP), and confounds analyses of the pharmacological effects of diphosphonucleotides. To examine the potential presence of ecto-nucleoside diphosphokinase activity in airway epithelial cells, [$^3$H]UDP was added to the mucosal surface in combination with ATP. These results are shown in FIG. 2C. [$^3$H]UTP was rapidly formed under these conditions, and similar results were obtained with either 0.1 μM or 100 μM [$^3$H]UDP. Comparable results also were obtained in experiments examining nucleoside diphosphokinase activity on the serosal side. Since potential ATP release from epithelial cells during tissue manipulations and consequential phosphorylation of UDP to UTP by nucleoside diphosphokinase may complicate study of the actions of UDP, hexokinase (2 U/mL) and glucose were included in all subsequent assays examining the effects of UDP, as explained above. No accumulation of [$^3$H]UTP occurred under these incubation conditions.

EXAMPLE 10

Activity of UDP at Human Nasal Epithelial Cell Surface

It has been established that primary cultures of polarized human airway epithelial cells express $P2Y_2$ receptors on both cell surfaces. S. J. Mason et al., *Br. J. Pharmacol.* 103, 1649–1656 (1991). It has also been reported that functional expression of the $P2Y_2$ receptor in polarized human nasal epithelial cells is asymmetric and that the receptor apparently couples more efficaciously to its effector phospholipase C on the serosal (basolateral) surface than on the mucosal (apical) surface. Paradiso et al., supra.

Figure 3A:
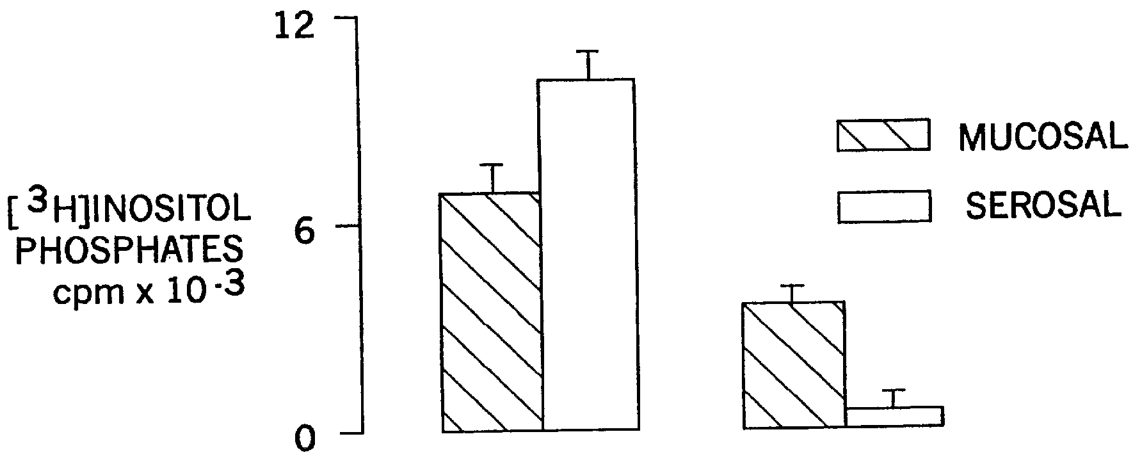
FIG. 3 is a schematic representation of the effects of UTP and UDP on $[^3H]$inositol phosphate formation in relation to either the mucosal or serosal cell surface.
Figure 3B:
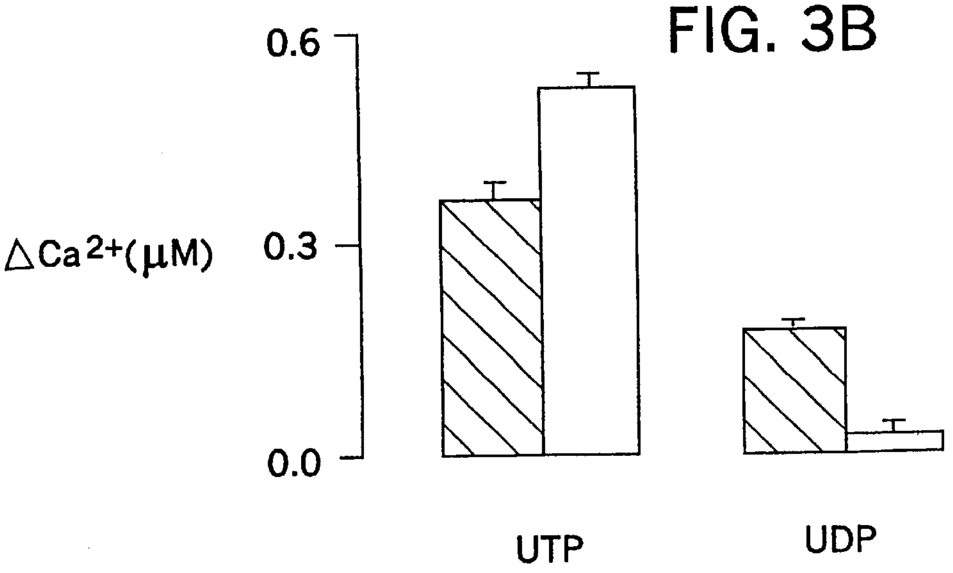

Consistent with this previous study, UTP (100 μM) promoted larger [$^3$H]inositol phosphate and calcium responses when applied to the basolateral bath of polarized primary human nasal epithelial cells, than when applied to the mucosal bath, as shown in FIGS. 3A and 3B. The results of FIGS. 3A and 3B were obtained after confluent cells were loaded with [$^3$H]myo-inositol and preincubated with LiCl (FIG. 3A, or with Fura-2 (FIG. 3B), as described above in Examples 2 and 3. The cells were challenged with 100 μM of the indicated nucleotide, added to either the serosal or the mucosal medium. The $Cl^-$ secretory responses ($\Delta I_{Cl^-}$) following addition of 100 μM UTP to either the mucosal or the serosal bath were 74±11 μA/cm$^2$ and 34±3 μA/cm$^2$, respectively. Application of UDP to the serosal bath had negligible effect on inositol phosphate accumulation.

Figure 4:
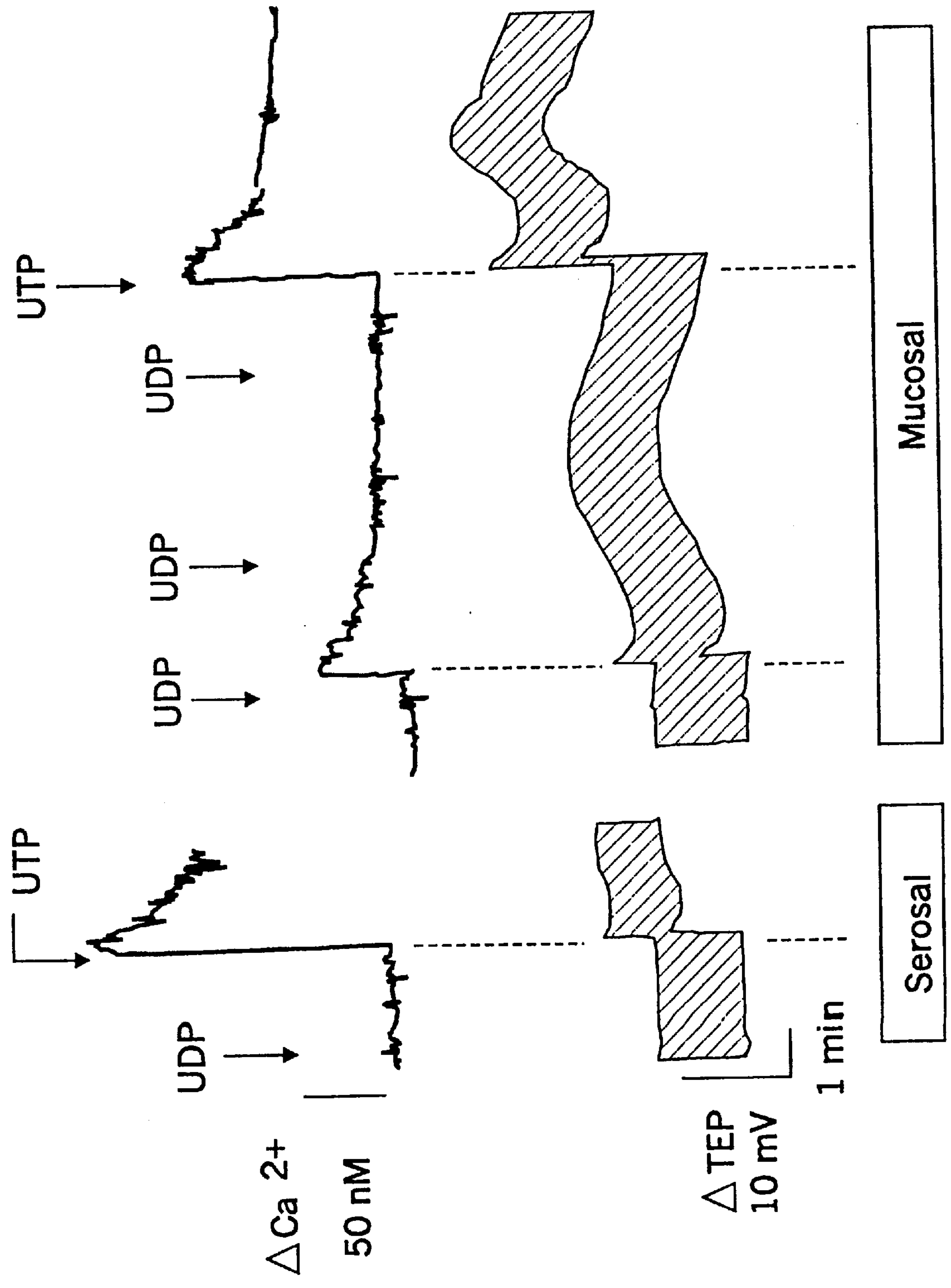
FIG. 4 consists of representative tracings of UDP- and UTP-promoted changes in intracellular $Ca^{2+}$ concentration and $Cl^-$ diffusion potentials in human nasal epithelial cells. The upper tracings show changes in intracellular $Ca^{2+}$ concentration on the serosal (left-hand tracing) and mucosal (right-hand tracing) after the addition of UDP and UTP to the cell surface medium, as indicated. The lower tracings illustrate changes of transepithelial potential difference (ΔTEP) on the serosal (left-hand tracing) and mucosal (right-hand tracing) after the addition of UDP and UTP to the cell surface medium, as indicated. The data are representative of at least eight independent experiments.

In contrast, mucosal UDP (100 μM) promoted marked accumulation of [$^3$H]inositol phosphates and calcium mobilization, and the maximal effects of UDP were approximately one half the magnitude of the responses observed with mucosal UTP, as shown in FIGS. 3 and 4. Similarly, mucosal but not serosal UDP stimulated $Cl^-$ secretion ($\Delta I_{Cl^-}$=16±3 μA·cm$^2$ for 3 μM mucosal UDP; $\Delta I_{Cl^-}$=0±0 μA·cm$^2$ for 3 μM serosal UDP) and the magnitude of this response was approximately one half of the mucosal UTP response (shown in FIG. 4). The effects of mucosal application of UDP cannot be explained by activation of $P2Y_2$ receptors since UTP-free UDP is essentially inactive at the $P2Y_2$ receptor (Nicholas et al., supra), and since UDP caused little or no effect when applied to the $P2Y_2$ receptor-expressing serosal side of the cell monolayers (FIGS. 3 and 4). The results in FIG. 4 were obtained after primary cultures of human nasal epithelial cells were mounted on modified Ussing chambers as detailed above in Example 3. Changes in $Ca^{2+}$ concentration (top tracings) or in $Cl^-$ secretion (bottom tracings) were simultaneously recorded after the addition to the basolateral medium of 100 μM UDP followed by 100 μM UTP (serosal), or after two consecutive additions of 3 μM UDP and then 10 μM UDP to the apical medium followed by the ipsilateral addition of 10 μM UTP (mucosal). The larger mucosal versus serosal effect of UDP contrasts with the predominantly basolateral effects of UTP (FIG. 3) and ATP. See, e.g., Paradiso et al., supra. Thus, the action of UDP in polarized airway epithelial cells does not coincide with that observed with $P2Y_2$ receptor agonists.

Figure 5:
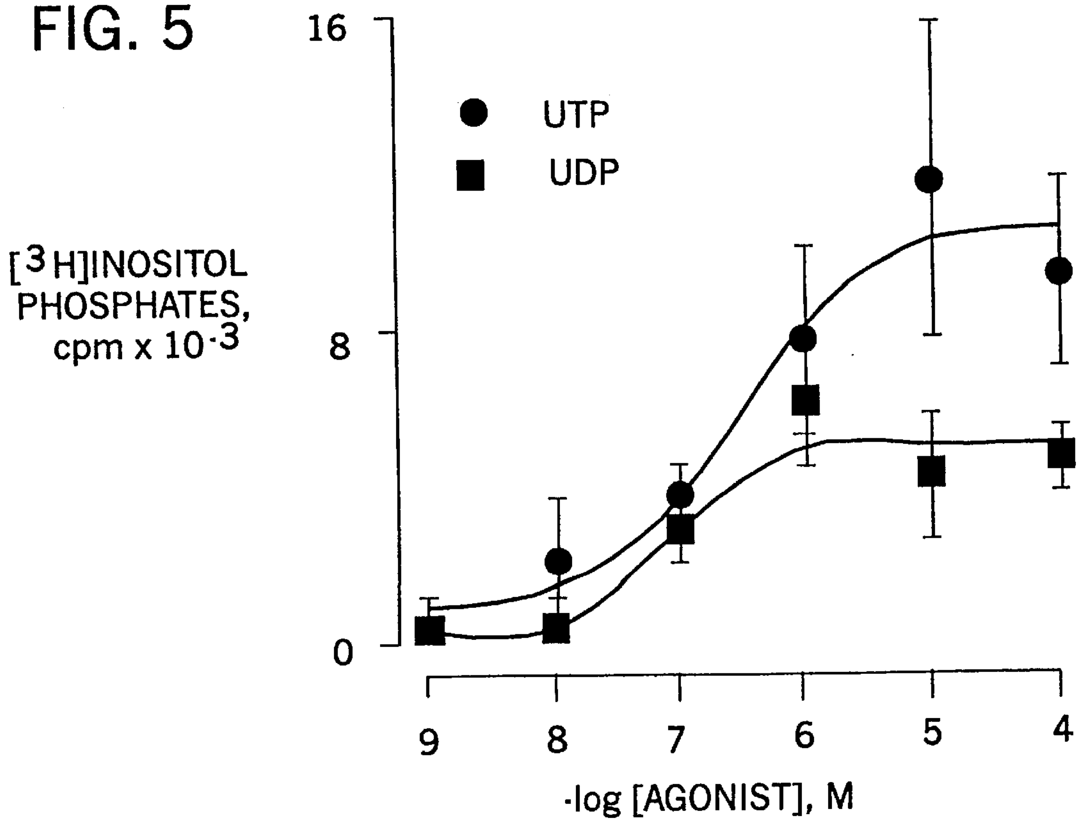
FIG. 5 is a graph illustrating the concentration-response relationship for mucosal UDP- and UTP-stimulated $[^3H]$ inositol phosphate formation in human nasal epithelial cells. The log-concentration of either UTP (filled-in circles, ●) or UDP (filled-in squares, ■) is indicated on the x-axis of the graph. The concentration of $[^3H]$inositol phosphates in units of cpm×$10^{-3}$M is indicated on the y-axis if the graph. The data represent the mean value (±S.E.M.) from three independent experiments performed with triplicate samples.

Although mucosal UDP was less efficacious than mucosal UTP in stimulating inositol phosphate formation in human nasal epithelium, UDP ($EC_{50}$=190±27 nM) and UTP ($EC_{50}$=280±35 nM) exhibited similar potencies, as shown in FIG. 5. The results in FIG. 5 were obtained after confluent cells were labeled with [$^3$H]myo-inositol, preincubated with LiCl as described above, and subsequently challenged for 10 min with the indicated concentration of UDP or UTP added to the mucosal medium. Cross-desensitization experiments were carried out to further address the hypothesis that UDP promotes signaling responses in airway cells through a receptor distinct from the $P2Y_2$ receptor. Addition of 3 μM UDP to the mucosal bath promoted mobilization of intracellular calcium with a $\Delta Ca^{2+}$ of 66±12 nM, and changes in $Cl^-$ secretory responses ($\Delta I_{Cl^-}$) of −16.3±3 μA/cm$^2$ (n=8). Subsequent addition of 3 μM UDP followed by 10 μM UDP did not result in elevation of intracellular $Ca^{++}$ ($\Delta Ca^{2+}$=0) or in $Cl^-$ secretion ($\Delta I_{Cl^-}$=0), which suggests the occurrence of UDP-induced desensitization (see FIG. 4). In contrast, responses to UTP (control cells, $\Delta Ca^{2+}$=374±24 nM [n=19]; $\Delta I_{Cl^-}$=−74±11 μA/cm$^2$ [n=12]; UDP-treated cells, $\Delta Ca^{2+}$=310±35 mM [n=8]; $\Delta_{Cl^-}$=−61±10 nM [n=8]) were retained. Responses to ATP also were retained following multiple additions of UDP.

EXAMPLE 11

Analysis of UDP Assay Results

The results presented above illustrate that although UDP is not a $P2Y_2$ receptor agonist, it nonetheless is a potent agonist at the human airway epithelial cell surface. The effects of UDP could not be attributed to contamination with UTP. Solutions of UDP were pre-incubated with hexokinase and glucose to eliminate any traces of UTP, and hexokinase and glucose were included in studies of epithelial cells to prevent metabolic conversion of UDP to UTP by cell surface nucleoside diphosphokinases and endogenously released ATP. HPLC analysis of UDP solutions before and after incubation with cells indicated the absence of UTP. The almost equal potency of UDP and UTP on the airway cells notably contrasts with the low apparent activity of UDP at $P2Y_2$ receptors. The asymmetry of the effect of UDP on polarized epithelium, with a preferred mucosal versus serosal activity, also contrasts with the predominant serosal effect of UTP (and ATP) in airway cells. Since UDP does not activate the epithelial cell $P2Y_2$ receptor, the explanation for the stimulatory effect of this diphosphate is the existence of a novel airway receptor that selectively recognizes UDP.

The potential implications of these results are two-fold. First, they demonstrate that in the presence of the apparently more abundant $P2Y_2$ receptor, assay conditions can be established that allow resolution of a receptor that is selectively activated by UDP. Specifically, hexokinase and glucose can be utilized to study effects of UDP in tissues where UDP-selective effects are otherwise masked by a prominent $P2Y_2$ receptor. Second, the asymmetry of the effects of UDP and UTP in polarized epithelial cells indicates different regulatory functions for the receptors recognizing these two nucleotides. Activators of receptors on the serosal surface may be released at distant sites and access receptors via the blood stream, whereas UDP, which acts exclusively on the mucosal side of airway epithelial cells, may be generated locally. However, mucosal UTP is hydrolyzed at a 2–3 fold faster rate than mucosal UDP, and consequently, UDP likely accumulates on the apical surface after the breakdown of UTP. Thus, released UTP could be an important source of extracellular UDP, which in turn potentially serves as a physiologically important signaling molecule in human airway tissue.

EXAMPLE 12

Effect of UDP on Mucociliary Clearance in Sheep

Figure 6:
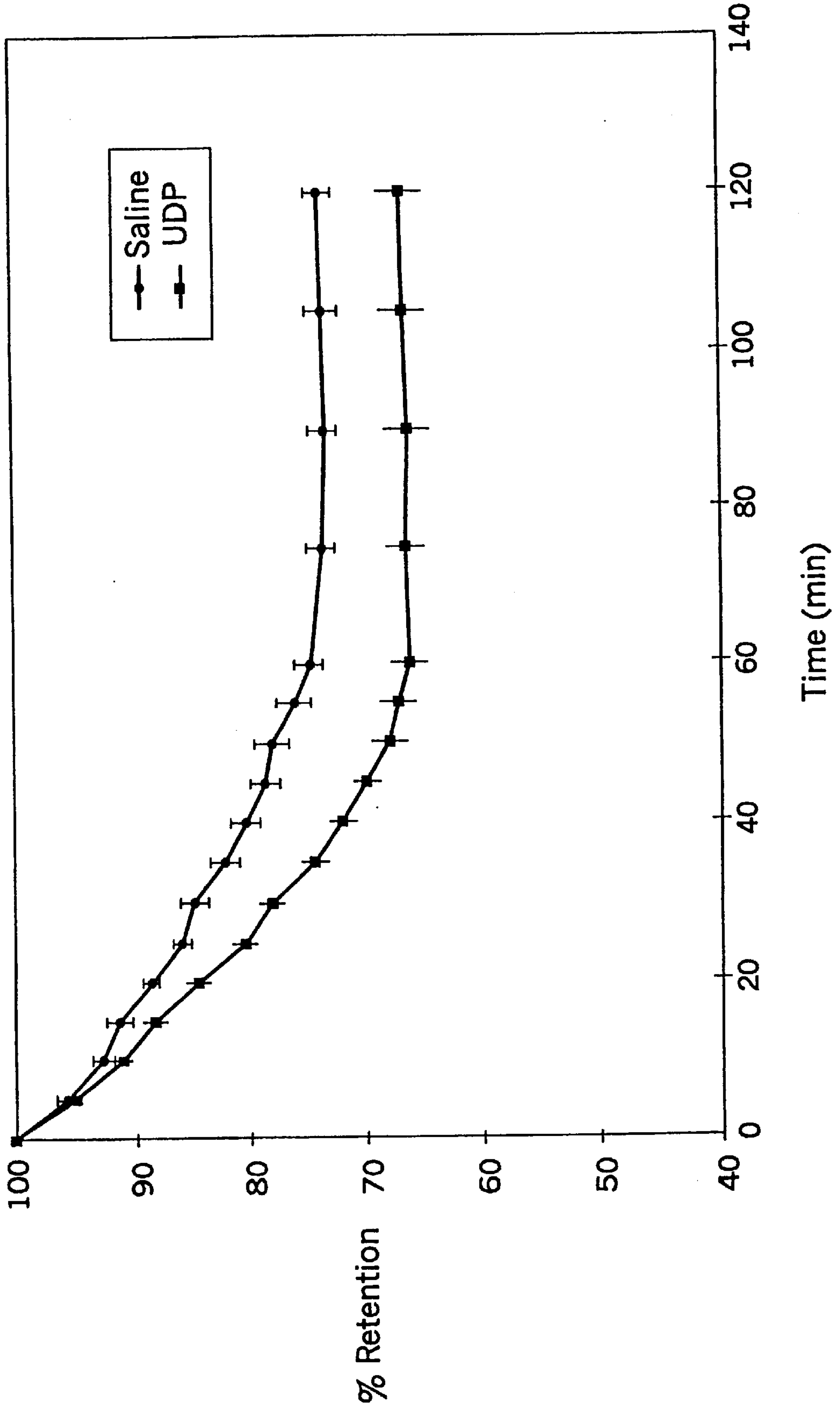
FIG. 6 is a graph illustrating the effects on mucociliary clearance in sheep after the administration of either a saline control (circles, ●) or UDP (squares, ■). Time in minutes after administration of the compound is indicated on the x-axis of the graph, while percentage retention of mucus is indicated on the y-axis.

Healthy adult ewes were given $^{99m}$Tc-labeled serum albumin ($^{99}$mTc-HCA) via a nebulized aerosol. The ($^{99m}$Tc-HCA) (20 mCi) was administered over 5 minutes through a nasotracheal tube introduced under local anesthesia with 2% lidocaine. After administration of the $^{99}$mTc-HCA, the animals were given the test compound UDP. The test compound was administered by nebulization in a volume of 4 mL over a period of 10–12 min. The test compound was given at a dose of 400 $\mu$mole. After the administration of the test compound, the animals were extubated. Clearance of the radiolabeled particles was monitored with a gamma camera. Measurements were made a 0, 5, 10, 15, 20, 25, 30, 35, 40, 45, 50, 55, 60, 75, 90, 105 and 120 minutes. Results of this study (n=7) have shown that the test compound promotes clearance of radiolabeled particles when compared to the saline control. The maximal effect for 400 $\mu$mole UDP was 33.6±1.6% clearance. The response to UDP was maximal at 60 minutes and was maintained for the second hour of the study. The results of this experiment are illustrated graphically in FIG. 6.

EXAMPLE 13

Effect of UDP on Tracheal Mucus Velocity in Sheep

To measure the effect of UDP on tracheal mucus velocity (TMV), the nasal passages of conscious adult ewes were anesthetized with a 2% lidocaine solution. After local anesthesia was produced, a modified endotracheal tube (7.5 mm) was placed such that the cuff was just below the vocal cords (as verified by fluoroscopy). Inspired air was warmed and humidified. The cuff on the endotracheal tube was inflated only during administration of the test compound to minimize possible impairment of TMV by the cuff. Test compounds were administered by nebulization in a volume of 4 mL over a period of 10–12 min.

TMV was measured by fluoroscopy. Ten to twenty radiopaque disks (Teflon/bismuth trioxide; 1 mm diameter; 0.8 mm thick, weighing 1.8 mg) were introduced into the trachea through a modified suction catheter with a puff of compressed air (3–4 L/min). Velocities of the individual disks were recorded on videotape form a portable image intensifier unit. Individual disk velocities were calculated by measuring the distance traveled by each disk during a 1 min observation period. Values reported are the means of the individual disk velocities. A collar was worn by the sheep, which was used as a standard to correct for magnification errors inherent in the fluoroscope.

Figure 7:
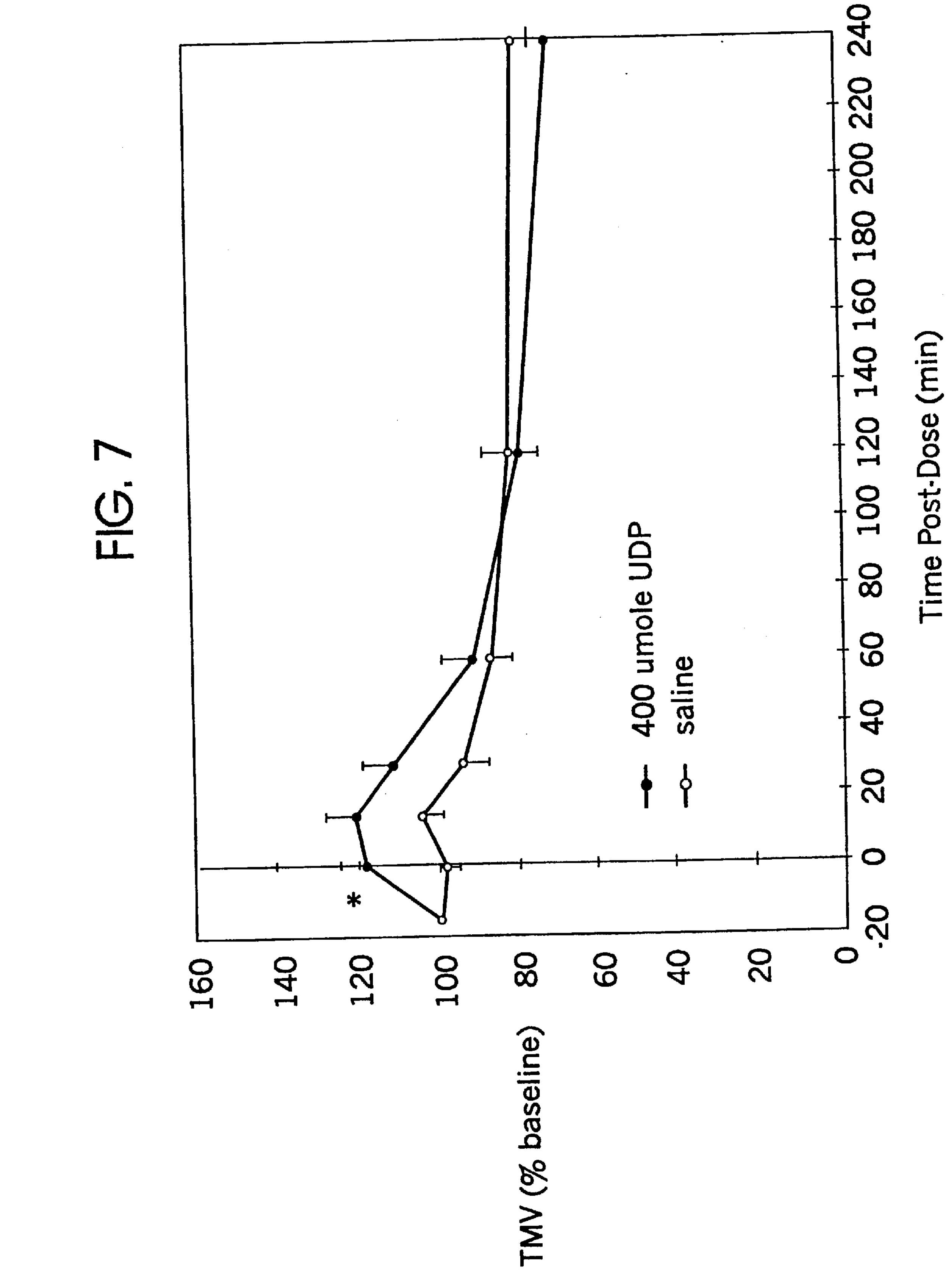
FIG. 7 is a graph illustrating the effects on tracheal mucus velocity (TMV) in sheep after the administration of either a saline control (open diamond ◇) or UDP (closed circle, ●). Time in minutes after administration of the compound is indicated on the x-axis of the graph, while TMV measured as a percentage of baseline is indicated on the y-axis.

UDP (400 $\mu$mole; 4 mL of a $10^{-1}$ $\mu$M) produced significant effects on tracheal mucus velocity. UDP produced a maximal effect of 121±8& of baseline (mean standard error, n=6). UDP produced its maximal effects 15 min after administration. However, when pairwise comparisons were made, only the time point immediately after dosing (t=0) was significantly different from the saline treatment group. The results of this experiment are illustrated graphically in FIG. 7.

EXAMPLE 14

Synthesis of UDP Analogs and $P2Y_6$ Activity of Analogs

The following method was used for measuring inositol phosphate accumulation of the UDP analogs described within this example as drugs. 1321N1 astrocytoma cells, stably overexpressing the human $P2Y_6$ receptor (Nicholas, et al., *Mol. Pharmacol.* 50, 224–229 (1996)), were seeded into 96 well plates (7500 cells/well) in DMEM-H supplemented with 10% FCS. After 48 hours, the growth media was replaced with inositol-free DMEM-H supplemented with 2.5% dialyzed FCS and [$^3$H]-inositol (0.2 uCi/well) to radiolabel hormone-responsive inositol phospholipid pools. Cells were stimulated 48 hours later. At the time of assay, the culture media was supplemented with 25 mM HEPES (pH 7.4) and 10 mM $LiCl_2$ to prevent hydrolysis of [$^3$H]-inositol phosphates. In addition, hexokinase (0.03 U/well) and glucose (50 mM final concentration) was added to the cultures to provide an enzymatic mechanism for the depletion of nucleoside triphosphates contaminating drug solutions or released from cells prior to/or during cell stimulation reactions. Drugs were diluted in phosphate buffered saline containing hexokinase/glucose and incubated at 37° for 30 minutes prior to addition to cells. Reactions were terminated after 60 minutes by rapid aspiration of media followed by the addition of ice cold EDTA (1.0 mM) and incubation on ice for at least 15 minutes prior to resolution of [$^3$H]-inositol phosphates by ion exchange chromatography as described (Brown, et. al., supra).

The drugs used in the assay described above were synthesized as follows:

(Compound A) 5-Methyluridine 5'-diphosphate

5-Methyluridine 5'-triphosphate (0.0047 g, 0.009 mMol) was dissolved in 0.7 mL 1M Tris buffer (pH 8.5 containing 1M $MgCl_2$) then 0.3 mL of a 0.25M glucose solution in 1M Tris buffer (pH 8.5 containing 1M $MgCl_2$) added. A $T_0$ timepoint was taken by reverse phase anion exchange HPLC. Hexokinase (EC 2.7.1.1, Boehringer Mannheim, from yeast overproducer), 75 units in 3.2M ammonium sulfate suspension, was added to the reaction which was incubated at 25° C. An HPLC was taken at 66 hours indicating complete conversion to diphosphate with no triphosphate remaining. Triphosphate retention: 17.5 minutes; diphosphate retention: 10.3 minutes.

The following nucleoside 5'-diphosphates were prepared by the same procedure as above, with modifications noted.

(Compound B) 4-Hexyloxyuridine 5'-diphosphate

Incubation for 21 days, diphosphate retention: 13.5 minutes.

(Compound C) N,N-dimethylcytidine 5'-diphosphate

Incubation for 30 days, diphosphate retention: 11.62 minutes.

(Compound D) 4-Methoxyuridine 5'-diphosphate

Incubation for 20 days, diphosphate retention: 10.76 minutes.

(Compound E) N-hexylcytidine 5'-diphosphate

Incubation for 12 days, diphosphate retention: 11.56 minutes.

(Compound F) 4-(N-morpholino)uridine 5'-diphosphate

Incubation for 21 days, diphosphate retention: 10.78 minutes.

(Compound G) 5-(Phenylethynyl)uridine 5'-diphosphate

Incubation for 48 hours, diphosphate retention: 13.91 minutes.

(Compound H) 3'-Deoxyuridine 5'-diphosphate

Incubation for 35 days, diphosphate retention: 8.0 minutes.

(Compound I) N-Cyclopentylcytidine 5'-diphosphate

Incubation for 6 days, diphosphate retention: 12.24 minutes.

(Compound J) 4-Hexylthiouridine 5'-diphosphate

Incubation for 4 days, diphosphate retention: 7.51 minutes.

Activity on $P2Y_6$ was measured as described above, with the following results:

| Activity on $P2Y_6$ ($EC_{50}$ in $\mu$Mol) | |
|---|---|
| Compound A: | 0.5 |
| Compound B: | 3.0 |
| Compound C: | 41.7 |
| Compound D: | 4.7 |
| Compound E: | 25.5 |
| Compound F: | 55.1 |
| Compound G: | 0.02 |
| Compound H: | 2.1 |
| Compound I: | 8.6 |
| Compound J: | 1.8 |

The foregoing Examples are illustrative of the present invention and are not to be construed as limiting thereof. Accordingly, the invention is defined by the following claims, with equivalents of the claims included therein.

That which is claimed:

1. A method of hydrating lung mucus secretions in the lungs of a subject in need of such treatment, comprising administering to the lungs of the subject a compound of Formula I below, or a pharmaceutically acceptable salt thereof, in an amount sufficient to hydrate lung mucus secretions:

(I)

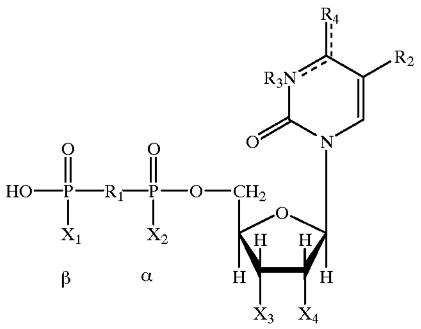

wherein:

$X_1$, and $X_2$ are each independently either $O^-$ or $S^-$;

$X_3$ and $X_4$ are each independently either —H or —OH, with the proviso that $X_3$ and $X_4$ are not simultaneously —H;

$R_1$ is selected from the group consisting of O, imido, methylene and dihalomethylene;

$R_2$ is selected from the group consisting of H, halo, alkyl, substituted alkyl, alkoxyl, nitro and azido;

$R_3$ is selected from the group consisting of H, alkyl, acyl, aryl, and arylalkyl; and $R_4$ is selected from the group consisting of —OR', —SR', —NR', and —NR'R", wherein R' and R" are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring.

2. A method according to claim 1, wherein said compound of Formula I is administered by delivering an aerosol suspension of respirable particles comprised of a compound of Formula I to the lungs of said subject.

3. A method according to claim 2, wherein said particles are selected from the group consisting of solid particles and liquid particles.

4. A method according to claim 2, wherein said aerosol is comprised of particles in the respirable range.

5. A method of treating cystic fibrosis in a human subject in need of such treatment, comprising administering by inhalation an aerosol suspension of respirable particles to the lungs of said subject, said particles comprised of Formula I, or a pharmaceutically acceptable salt thereof:

(I)

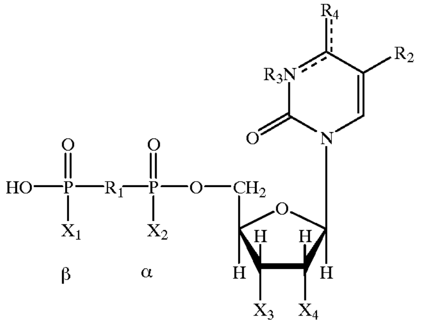

wherein:

$X_1$, and $X_2$ are each independently either $O^-$ or $S^-$;

$X_3$ and $X_4$ are each independently either —H or —OH, with the proviso that $X_3$ and $X_4$ are not simultaneously —H;

$R_1$ is selected from the group consisting of O, imido, methylene and dihalomethylene;

$R_2$ is selected from the group consisting of H, halo, alkyl, substituted alkyl, alkoxyl, nitro and azido;

$R_3$ is selected from the group consisting of H, alkyl, acyl, aryl, and arylalkyl; and $R_4$ is selected from the group consisting of —OR', —SR', —NR', and —NR'R", wherein R' and R" are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring;

and wherein said particles are administered in an amount effective to treat said cystic fibrosis in said subject.

6. A method according to claim 5, wherein said particles are selected from the group consisting of solid particles and liquid particles.

7. A method according to claim 6, wherein said aerosol is comprised of particles having a particle size within the respirable range.

8. A method according to claim 5, further comprising concurrently administering to said subject a compound selected from the group consisting of amiloride, benzamil, and phenamil.

9. A method of treating primary ciliary dyskinesia in a human subject in need of such treatment, comprising administering by inhalation an aerosol suspension of respirable particles to the lungs of said subject, said particles comprised of Formula I, or a pharmaceutically acceptable salt thereof:

(I)

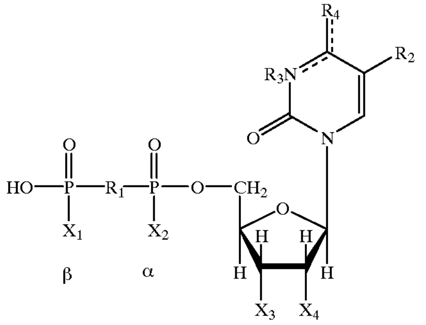

wherein:

$X_1$, and $X_2$ are each independently either $O^-$ or $S^-$;

$X_3$ and $X_4$ are each independently either —H or —OH, with the proviso that $X_3$ and $X_4$ are not simultaneously —H;

$R_1$ is selected from the group consisting of O, imido, methylene and dihalomethylene;

$R_2$ is selected from the group consisting of H, halo, alkyl, substituted alkyl, alkoxyl, nitro and azido;

$R_3$ is selected from the group consisting of H, alkyl, acyl, aryl, and arylalkyl; and $R_4$ is selected from the group consisting of —OR', —SR', —NR', and —NR'R", wherein R' and R" are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring;

and wherein said particles are administered in an amount effective to treat said primary ciliary dyskinesia in said subject.

10. A method according to claim 9, wherein said particles are selected from the group consisting of solid particles and liquid particles.

11. A method according to claim 10, wherein said aerosol is comprised of particles having a particle size within the respirable range.

12. A method according to claim 9, further comprising concurrently administering to said subject a compound selected from the group consisting of amiloride, benzamil, and phenamil.

13. A method of treating chronic obstructive pulmonary disorder in a human subject in need of such treatment, comprising administering by inhalation an aerosol suspension of respirable particles to the lungs of said subject, said particles comprised of Formula I, or a pharmaceutically acceptable salt thereof:

(I)

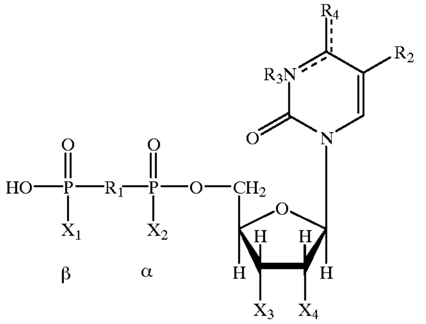

wherein:

$X_1$, and $X_2$ are each independently either $O^-$ or $S^-$;

$X_3$ and $X_4$ are each independently either —H or —OH, with the proviso that $X_3$ and $X_4$ are not simultaneously —H;

$R_1$ is selected from the group consisting of O, imido, methylene and dihalomethylene;

$R_2$ is selected from the group consisting of H, halo, alkyl, substituted alkyl, alkoxyl, nitro and azido;

$R_3$ is selected from the group consisting of H, alkyl, acyl, aryl, and arylalkyl; and $R_4$ is selected from the group consisting of —OR', —SR', —NR', and —NR'R", wherein R' and R" are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring;

and wherein said particles are administered in an amount effective to treat said chronic obstructive pulmonary disorder in said subject.

14. A method according to claim 13, wherein said particles are selected from the group consisting of solid particles and liquid particles.

15. A method according to claim 14, wherein said aerosol is comprised of particles having a particle size within the respirable range.

16. A method according to claim 13, further comprising concurrently administering to said subject a compound selected from the group consisting of amiloride, benzamil, and phenamil.

17. A method of treating ventilator-associated pneumonia in a human subject in need of such treatment, comprising administering by inhalation an aerosol suspension of respirable particles to the lungs of said subject, said particles comprised of Formula I, or a pharmaceutically acceptable salt thereof:

(I)

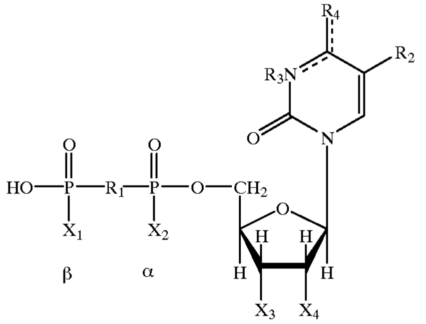

wherein:

$X_1$, and $X_2$ are each independently either $O^-$ or $S^-$;

$X_3$ and $X_4$ are each independently either —H or —OH, with the proviso that $X_3$ and $X_4$ are not simultaneously —H;

$R_1$ is selected from the group consisting of O, imido, methylene and dihalomethylene;

$R_2$ is selected from the group consisting of H, halo, alkyl, substituted alkyl, alkoxyl, nitro and azido;

$R_3$ is selected from the group consisting of H, alkyl, acyl, aryl, and arylalkyl; and $R_4$ is selected from the group consisting of —OR', —SR', —NR', and —NR'R", wherein R' and R" are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring;

and wherein said particles are administered in an amount effective to treat said ventilator-associated pneumonia in said subject.

18. A method according to claim 17, wherein said particles are selected from the group consisting of solid particles and liquid particles.

19. A method according to claim 18, wherein said aerosol is comprised of particles having a particle size within the respirable range.

20. A method according to claim 17, further comprising concurrently administering to said subject a compound selected from the group consisting of amiloride, benzamil, and phenamil.

21. A method of treating chronic bronchitis in a human subject in need of such treatment, comprising administering by inhalation an aerosol suspension of respirable particles to the lungs of said subject, said particles comprised of Formula I, or a pharmaceutically acceptable salt thereof:

(I)

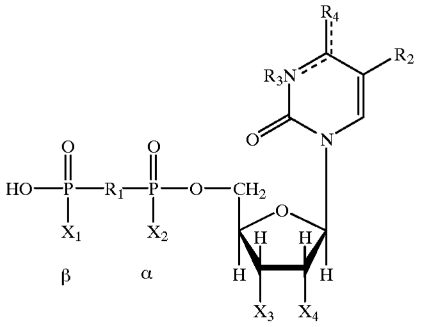

wherein:

$X_1$, and $X_2$ are each independently either $O^-$ or $S^-$;

$X_3$ and $X_4$ are each independently either —H or —OH, with the proviso that $X_3$ and $X_4$ are not simultaneously —H;

$R_1$ is selected from the group consisting of O, imido, methylene and dihalomethylene;

$R_2$ is selected from the group consisting of H, halo, alkyl, substituted alkyl, alkoxyl, nitro and azido;

$R_3$ is selected from the group consisting of H, alkyl, acyl, aryl, and arylalkyl; and $R_4$ is selected from the group consisting of —OR', —SR', —NR', and —NR'R", wherein R' and R" are independently selected from the group consisting of H, alkyl, substituted alkyl, aryl, substituted aryl, arylalkyl, alkoxyl, and aryloxyl, and with the proviso that R' is absent when $R_4$ is double bonded from an oxygen or sulfur atom to the carbon at the 4-position of the pyrimidine ring;

and wherein said particles are administered in an amount effective to treat said chronic bronchitis in said subject.

22. A method according to claim 21, wherein said particles are selected from the group consisting of solid particles and liquid particles.

23. A method according to claim 22, wherein said aerosol is comprised of particles having a particle size within the respirable range.

24. A method according to claim 21, further comprising concurrently administering to said subject a compound selected from the group consisting of amiloride, benzamil, and phenamil.

* * * * *